United States Patent
Clokie et al.

(10) Patent No.: US 6,287,312 B1
(45) Date of Patent: Sep. 11, 2001

(54) ORAL CRANIOFACIAL BONE MILL

(76) Inventors: Cameron M. L. Clokie, 40 Blyth Hill Road, Toronto Ontario (CA), M4N 3L7; Ariel R. Dujovne, 5712 Hudson Avenue, Côte St. Luc Quebec (CA), H4W 2K5

(*) Notice: Subject to any disclaimer, the term of this patent is extended or adjusted under 35 U.S.C. 154(b) by 0 days.

(21) Appl. No.: 09/521,849

(22) Filed: Mar. 9, 2000

Related U.S. Application Data

(60) Provisional application No. 60/123,709, filed on Mar. 10, 1999.

(51) Int. Cl.$^7$ ..................................................... A61B 17/00
(52) U.S. Cl. ................................................................ 606/85
(58) Field of Search ................................ 606/85; 241/27, 241/606, 285.2, 100

(56) References Cited

U.S. PATENT DOCUMENTS

| | | | |
|---|---|---|---|
| 4,004,742 | * 1/1977 | Hess | 241/82.5 |
| 4,547,912 | * 10/1985 | Sherva-Parker | 623/16 |
| 4,699,325 | * 10/1987 | Hess | 241/82.5 |
| 5,769,853 | 6/1998 | Quétin | |
| 5,918,821 | 7/1999 | Grooms et al. | |

OTHER PUBLICATIONS

Micro–Knochenmühle Bone Mill.

* cited by examiner

Primary Examiner—Jeffrey A. Smith
Assistant Examiner—Eduardo C. Robert
(74) Attorney, Agent, or Firm—Swabey Ogilvy Renault

(57) ABSTRACT

A bone mill comprising a vessel and a rotatable grinding tool to produce ground autologous bone particles for surgical bone reconstruction use, wherein the vessel includes a wall defining a circular cylindrical chamber having a concentric axis. The vessel further includes a bottom wall at right angle to the axis and a lid adapted to be removably connected to the vessel. The lid includes an opening coincident with the axis. The grinding tool includes an elongated shaft extending through the opening in the lid along the axis with a cutting blade mounted to the shaft within the chamber whereby the cutting blade can be rotated by motive device, such as a dental drill, engaging the shaft exterior of the vessel to cut bone, placed in the vessel, into said bone particles.

11 Claims, 2 Drawing Sheets

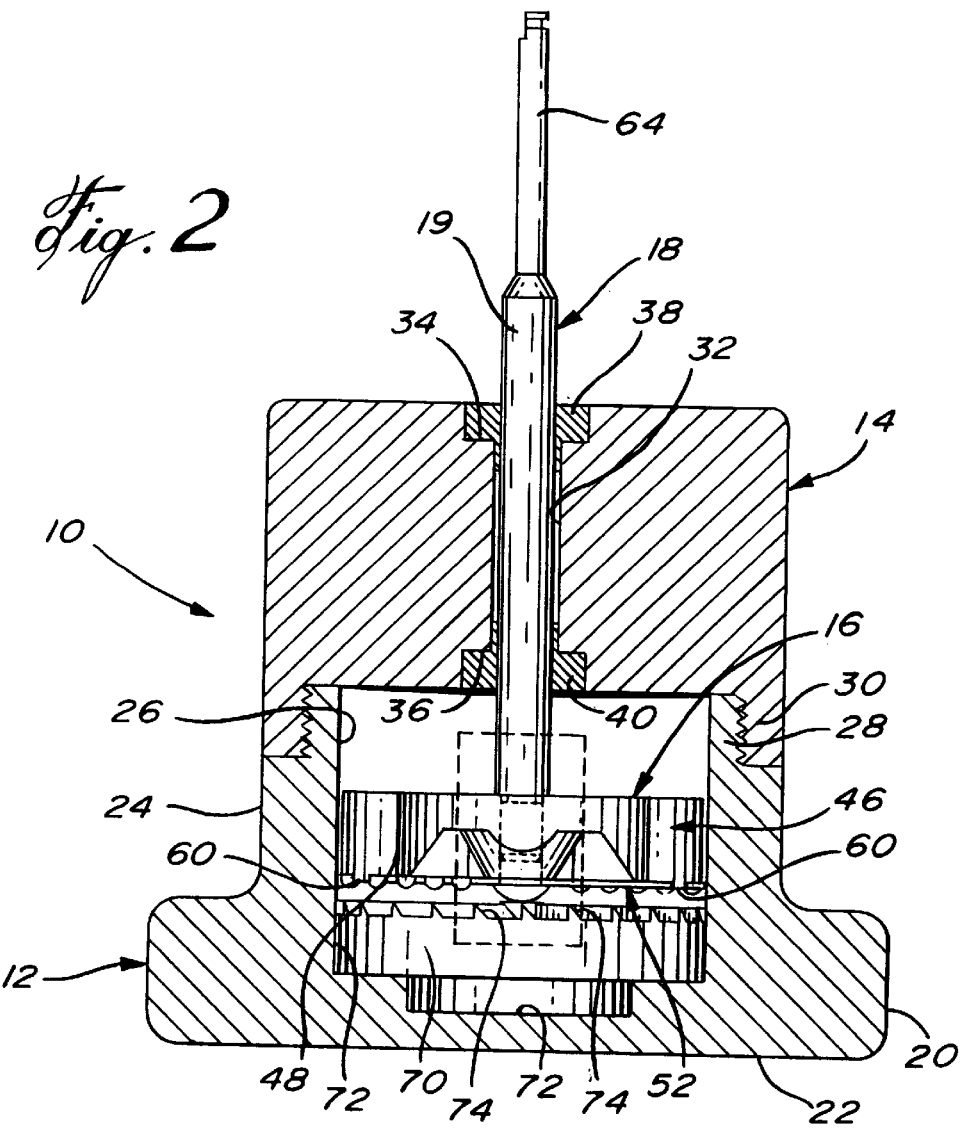
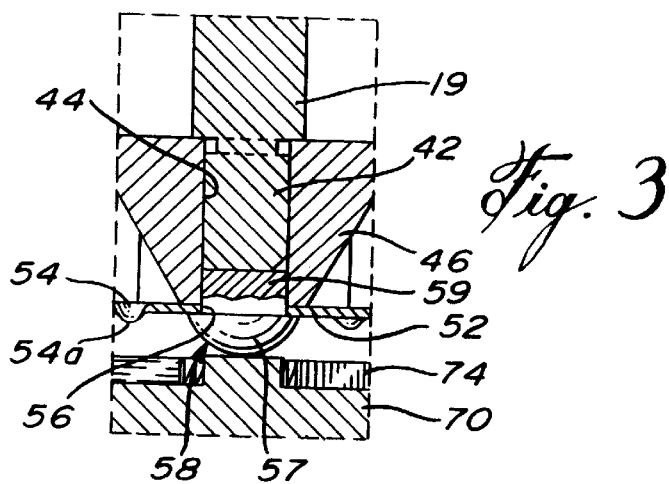

ORAL CRANIOFACIAL BONE MILL

This Application claim benefit to provisional Application 60/123,709 Mar. 10, 1999.

BACKGROUND OF THE INVENTION

1. Field of the Invention

The present invention relates to a bone grinding apparatus and, more particularly, to a portable bone mill for use in autologous bone grafts.

2. Description of the Prior Art

Bone grinders or bone mills have been developed in the recent past to allow surgeons, particularly when dealing with oral/maxillofacial, orthopedic, periodontal, and implant applications, to perform autologous bone grafts using autogenous bone from local reservoirs. Such bone mills allow the patient to have his or her own bone particles implanted when there is a preference to using autograft to address concerns over the possibility of rejection or infection. For instance, in an oral/maxillofacial intervention, the surgeon can use bone from the patient's mandibular symphysis or ramus, then grind the bone with the bone mill, and then utilize the bone particles to repair small bone defects and to achieve bone augmentation. Such procedures reduce the costs of surgery compared where other products, such as HA granules, processed coral, or freeze-dried bone are used.

U.S. Pat. No. 5,769,853, Quétin, issued Jun. 23, 1998, and U.S. Pat. No. 5,918,821, Grooms et al, issued Jul. 6, 1999, are representative of bone grinders or mills which can produce small bone particles for the purpose of autologous bone grafts.

In the light of the existing bone mills as represented by these patents and others available in the marketplace, there is a need for a simple, power-driven bone mill which can be easily utilized in a surgical environment, using the power tools available.

SUMMARY OF THE INVENTION

It is an aim of the present invention to provide a bone mill having a simple construction and adapted to be operated by available power tools, such as a dental power drill.

It is a further aim of the present invention to provide a hygienic simple bone mill utilizing a one-use milling or cutting blade which can be easily replaced.

It is a further aim of the present invention to provide a portable bone mill which can be hand-held or clamped on a flat surface during operation.

A construction in accordance with the present invention comprises a bone mill including a vessel and a rotatable grinding tool to produce ground autologous bone particles for surgical bone reconstruction use, wherein the vessel includes a wall defining a circular cylindrical chamber having a concentric axis, the vessel further including a bottom wall at right angle to the axis, a lid adapted to be removably connected to the vessel, the lid including an opening coincident with the axis, the grinding tool including an elongated shaft extending through the opening in the lid along the axis, a cutting blade mounted to an end of the shaft within the chamber whereby the cutting blade can be rotated by motive means engaging the shaft, exterior of the vessel, to cut bone, placed in the vessel, into said bone particles.

In a preferred embodiment of the present invention, a bone mill comprises a vessel and a rotatable grinding tool to produce ground autologous bone particles for surgical bone reconstruction use, wherein the vessel includes a wall defining a circular cylindrical chamber having a concentric axis, the vessel further including a bottom wall at right angle to the axis, a lid adapted to be removably connected to the vessel, the lid including an opening coincident with the axis, the grinding tool including an elongated shaft extending through the opening in the lid along the axis, the lid including bearing means for the shaft of the grinding tool to permit the shaft to rotate on the axis, a cutting blade mounted to an end of the shaft within the chamber and a bone gripping plate on the bottom wall whereby the cutting blade can be rotated by motive means engaging the shaft, exterior of the vessel, to cut bone, placed in the vessel against the bone gripping plate, into said bone particles.

More specifically, the bone mill includes a one-use cutting blade which is removably mounted to a blade support mounted to the end of the shaft within the vessel, and a blade retention member extends through a central opening in the blade and engages the support means. It is contemplated that the cutting blade could be fixed to the shaft. The whole grinding tool could be made as a one-use tool.

Still more specifically, the blade is in the form of a thin plate having rasp openings defined by rasp cutting edges for cutting the bone against the gripping plate and passing bone particles through the rasp openings in the cutting blade within the chamber opposite to the gripping plate.

BRIEF DESCRIPTION OF THE DRAWINGS

Having thus generally described the nature of the invention, reference will now be made to the accompanying drawings, showing by way of illustration, a preferred embodiment thereof, and in which:

FIG. 2 is an axial cross-section of the embodiment of the bone mill shown in FIG. 1; and FIG. 3 is an enlarged, fragmentary, cross-section of a detail shown in FIG. 2.

DESCRIPTION OF THE PREFERRED EMBODIMENTS

Figure 1:
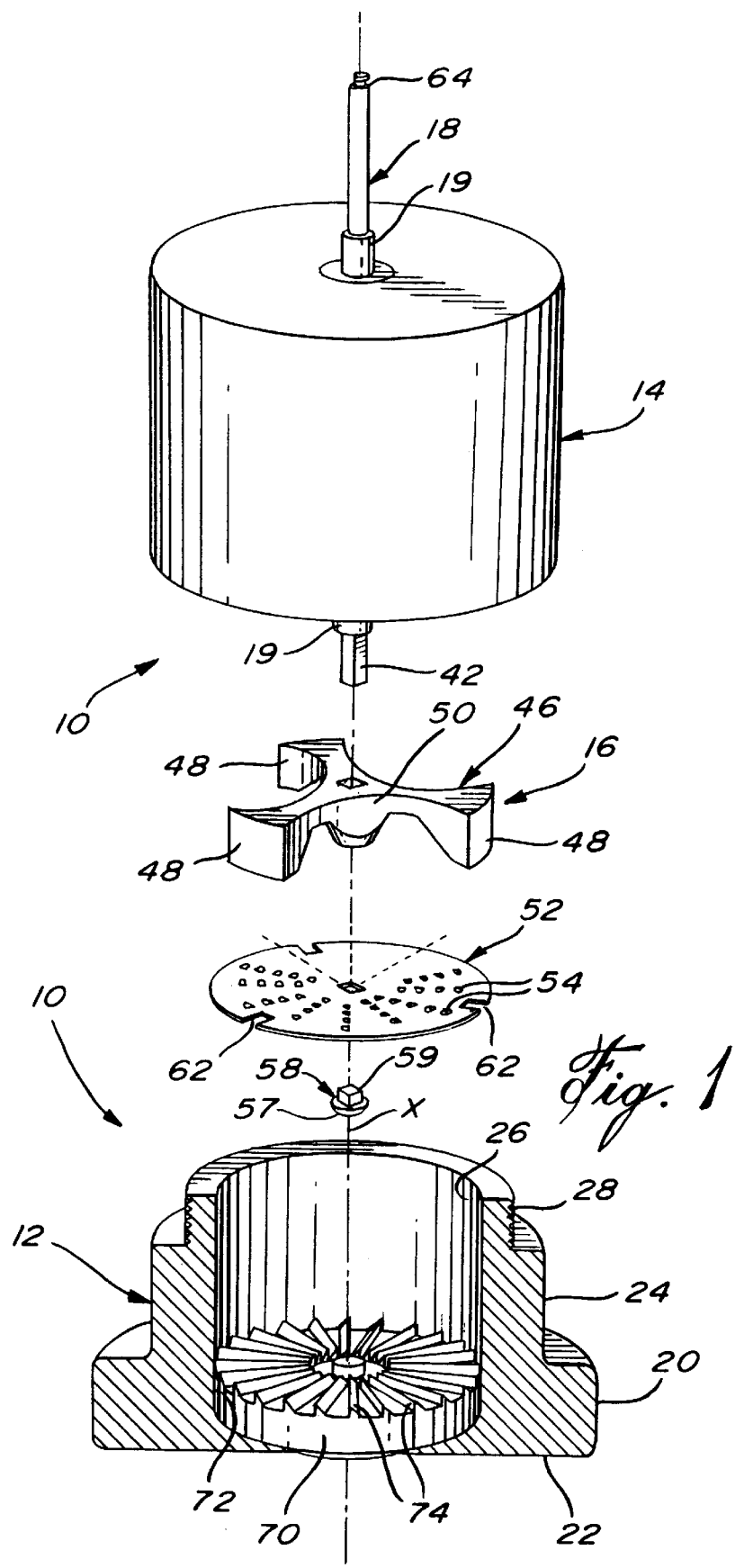
FIG. 1 is a perspective, exploded, fragmentary view showing a bone mill in accordance with the present invention.

Referring to FIGS. 1 and 2, the bone mill 10 is shown including a vessel 12 and a lid 14. A grinding tool 16 including a shaft 18 extends through the lid into the vessel 12.

The vessel includes a base 20 with a flat surface 22. A cylindrical wall 24 extends from the base 20 and defines a cylindrical chamber 26 having an axis X concentric with the cylindrical chamber 26. The cylindrical wall 24 includes a threaded segment 28 adapted to receive the lid 14 having a mating, threaded, cylindrical wall portion 30.

The lid includes a bore 32 with countersunk recesses 34 and 36 communicating with either end of the bore 32. Bearing sleeves 38 and 40 are inserted in the countersunk recesses 34 and 36 respectively.

The shaft 18 of the grinding tool 16 includes a larger diameter body portion 19 adapted to fit for rotational movement in the bore 32 against bushing sleeves 38 and 40. The end of the shaft 18 (FIG. 3) includes a square segment 42. A blade support 46 comprises a hub 50 with a socket 44 having a square cross-section and adapted to tightly fit on the square segment 42 of shaft 18. The blade support 46 has three legs 48 extending radially from the hub 50.

The cutting blade 52 is a circular thin blade having rasp openings 54 with rasp leading edges 54a similar to a cheese rasp. The cutting blade 52 has a square central opening 56 and a fastener 58 having a head 57 and a square shank 59 which passes through the square opening 56 and is tight-fitted in the square socket 44 in the hub 50, abutting against the end of square segment 42 of shaft 18. The blade support 46 includes square tabs 60 at the end of the legs 48 to engage openings 62 provided on the periphery of the cutting blade 52. The cutting blade 52 may be made of a #420 stainless steel. The blade 52 is a one-use blade and is easily removed from the support and is held there by the fastener 58. The blade 52 is also interchangeable so that different rasp sizes are provided depending on the size of the bone particles which are to be produced. Bone particles between 50 and 500 microns may be produced, and particles between 250 and 500 microns are preferred.

The other end 64 of shaft 18 is adapted to be engaged by the air drill used by dentists, for instance. Other drill tools could be used for rotating the shaft 18. The shaft preferably would be rotated between 500 and 5,000 rpm with a torque of between 60 and 100 newton/m.

A disc 70 of hard metal, such as stainless steel, is removably inserted in a recess 72 formed on the bottom wall 20 within the chamber 26. The disc 70 includes radially extending, uninterrupted ridges 74 which are ramp-shaped so that the leading edge of the ramp counters the rotational direction of the cutting tool 16. The ridges 74 help to retain the bone pieces while the grinding tool 16 is rotated. The shaft 18 and the cutting tool 16 can be moved axially, but the head 57 of the fastener 58 is dimensioned such that it will abut the central portion 76 of the disc 70 and allow a space between the rasp cutting edges 54a of the cutting blade 52 and the ridges 74 on the disc 70.

In operation, pieces of freshly removed bone are placed within the vessel 12, in the chamber 26 on the disc 70. The lid 14, including the grinding tool 16, is then placed on the vessel 12 with the cutting tool 16 in the chamber 26. The lid 14 is rotated so that it threadably engages the vessel 12. The shaft 18 is then connected to a power source, such as a dental drill, and the shaft 18 is rotated, thereby rotating the blade support 46 and the cutting blade 52. The cutting blade 52 rotates as the cutting tool 16 is advanced axially against the bone pieces on the disc 70. As the bone pieces are ground or cut up, the particles pass through the rasp openings 54 in the cutting blade 52 and are stored between the cutting blade 52 and the lid 14 within the chamber 26.

When there is little resistance felt on the grinding tool 16, the dental drill is disconnected from the shaft 18, and the lid 14 is removed from the vessel 12. The fastener 58 is then disconnected from the blade support 46 and the cutting blade 52 removed and discarded after the bone particles have been retrieved. The bone particles with blood and some tissue will remain in a glob and can be easily removed from the vessel 12.

The bone mill is then cleaned and a new blade 52 placed on the blade support 46.

The grinding tool 16 comprising the shaft, blade support, and cutting blade could be provided as a single assembled part. It is contemplated that the grinding tool 16 could be a single-use unit.

What is claimed is:

1. A bone mill comprising a vessel and a rotatable grinding tool to produce ground autologous bone particles for surgical bone reconstruction use, wherein the vessel includes a wall defining a circular cylindrical chamber having a concentric axis, the vessel further including a bottom wall at right angle to the axis, a lid adapted to be removably connected to the vessel, the lid including an opening coincident with the axis, the grinding tool including an elongated shaft extending through the opening in the lid along the axis, a cutting blade mounted to the shaft within the chamber whereby the cutting blade can be rotated by motive means engaging the shaft exterior of the vessel to cut bone, placed in the vessel, into said bone particles.

2. A bone mill comprising a vessel and a rotatable grinding tool to produce ground autologous bone particles for surgical bone reconstruction use, wherein the vessel includes a wall defining a circular cylindrical chamber having a concentric axis, the vessel further including a bottom wall at right angle to the axis, a lid adapted to be removably connected to the vessel, the lid including an opening coincident with the axis, the grinding tool including an elongated shaft extending through the opening in the lid along the axis, the lid including bearing means for the shaft of the grinding tool to permit the shaft to rotate on the axis, a cutting blade mounted to the shaft within the chamber and a bone gripping plate on the bottom wall whereby the cutting blade can be rotated by motive means engaging the shaft exterior of the vessel to cut bone, placed in the vessel against the bone gripping plate, into said bone particles.

3. The bone mill as defined in claim 2, wherein the cutting blade is a thin circular blade with rasp openings and cutting edges, a blade support member is mounted to an end of the shaft within the vessel, and the cutting blade is mounted to the blade support member whereby the blade is rotated for cutting bone against the gripping plate whereby bone particles pass through the rasp openings into the portion of the chamber between the cutting blade and the lid.

4. The bone mill as defined in claim 3, wherein the cutting blade is a one-use blade removably attached to the blade support.

5. The bone mill as defined in claim 4, wherein the blade support includes a hub mounted for rotation at the end of the shaft within the vessel, and three arms extend from the hub to engage the periphery of the blade so as to provide axial support to the blade.

6. The bone mill as defined in claim 4, wherein the means for removably attaching the cutting blade to the end of the shaft includes a fastener having a head and a shank, whereby the shank is adapted to engage the support member, and the head has an axial dimension which corresponds to the minimum spacing preferred between the cutting blade and the gripping plate during the operation of the bone mill.

7. The bone mill as defined in claim 3, wherein the cutting blade is removably connected to the end of the shaft and is interchangeable with other cutting blades where the rasps are of different sizes for producing different sized bone particles.

8. The bone mill as defined in claim 2, wherein the gripping plate is a hard metal disc removably supported in a recess formed in the bottom wall, and the gripping plate includes elongated, radially uninterrupted ridges.

9. The bone mill as defined in claim 2, wherein the shaft includes an end portion exterior of the vessel adapted to be engaged by a dental drilling tool providing rotation to the shaft and therefore the cutting blade.

10. The bone mill as defined in claim 9, wherein the shaft is rotated at a velocity between 500 and 5,000 rpm with between 60 to 100 newton/m of torque.

11. The bone mill as defined in claim 2, wherein the lid includes a bearing portion co-extensive with the axis in the vessel for providing stability to the shaft while allowing low friction rotation to the shaft.

* * * * *